(12) United States Patent
Grossman et al.

(10) Patent No.: US 10,088,894 B2
(45) Date of Patent: Oct. 2, 2018

(54) IMPLANTED DEVICES AND RELATED USER INTERFACES

(71) Applicant: Autodesk, Inc., San Rafael, CA (US)

(72) Inventors: Tovi Grossman, Toronto (CA); George Fitzmaurice, Toronto (CA); Anne Agur, Toronto (CA); Christian Holz, Berlin (DE)

(73) Assignee: AUTODESK, INC., San Rafael, CA (US)

( * ) Notice: Subject to any disclaimer, the term of this patent is extended or adjusted under 35 U.S.C. 154(b) by 205 days.

(21) Appl. No.: 13/715,916

(22) Filed: Dec. 14, 2012

(65) Prior Publication Data

US 2013/0176207 A1    Jul. 11, 2013

Related U.S. Application Data

(60) Provisional application No. 61/576,262, filed on Dec. 15, 2011.

(51) Int. Cl.

| | |
|---|---|
| *G06F 3/01* | (2006.01) |
| *G01C 17/00* | (2006.01) |
| *A61N 1/375* | (2006.01) |
| *G04G 9/04* | (2006.01) |
| *G04G 21/02* | (2010.01) |
| *A61F 2/02* | (2006.01) |

(Continued)

(52) U.S. Cl.
CPC ............. *G06F 3/011* (2013.01); *A61N 1/375* (2013.01); *G01C 17/00* (2013.01); *G04G 9/04* (2013.01); *G04G 21/02* (2013.01); *A61F 2/02* (2013.01); *A61N 1/3785* (2013.01); *H04M 1/0202* (2013.01)

(58) Field of Classification Search
CPC ......... A61F 2/02; A61N 1/375; A61N 1/3785; G04G 21/02; G04G 9/04; G06F 3/011; H04M 1/0202
See application file for complete search history.

(56) References Cited

U.S. PATENT DOCUMENTS 4,871,351 A  * 10/1989  Feingold ...................... 604/66
6,980,864 B2 * 12/2005  Faltys et al. ................. 607/116

(Continued)

FOREIGN PATENT DOCUMENTS

| CN | 101291634 A | 10/2008 |
|---|---|---|
| CN | 101689095 A | 3/2010 |

OTHER PUBLICATIONS

Yang et al., Distributed Recognition of Human Actions Using Wearable Motion Sensor Networks, Journal of Ambient Intelligence and Smart Environments 1 (2009) 1-5, IOS Press.*

(Continued)

*Primary Examiner* — Viet Pham
(74) *Attorney, Agent, or Firm* — Artegis Law Group, LLP

(57) ABSTRACT

Embodiments of the invention generally relate to electronic devices capable of being implanted beneath the skin of a human user. The electronic devices include input devices for receiving input from a user, and output devices for output signals or information to a user. The electronic devices may optionally include one or more sensors, batteries, memory units, and processors. The electronic devices are protected by a protective packaging to reduce contact with bodily fluids and to mitigate physiological responses to the implanted devices.

21 Claims, 4 Drawing Sheets

(51) Int. Cl.
*H04M 1/02* (2006.01)
*A61N 1/378* (2006.01)

(56) References Cited

U.S. PATENT DOCUMENTS

| | | | |
|---|---|---|---|
| 7,447,533 B1* | 11/2008 | Fang et al. | 600/310 |
| 7,571,002 B2 | 8/2009 | Thrope et al. | |
| 7,813,809 B2 | 10/2010 | Strother et al. | |
| 7,890,180 B2 | 2/2011 | Quiles | |
| 8,046,081 B2 | 10/2011 | Zierhofer et al. | |
| 2003/0208113 A1* | 11/2003 | Mault | A61B 5/14532 600/316 |
| 2004/0106955 A1* | 6/2004 | Swerdlow et al. | 607/7 |
| 2005/0278000 A1* | 12/2005 | Strother et al. | 607/48 |
| 2005/0288600 A1* | 12/2005 | Zhang et al. | 600/510 |
| 2006/0122661 A1* | 6/2006 | Mandell | 607/42 |
| 2007/0032837 A1* | 2/2007 | Thrope et al. | 607/48 |
| 2007/0287892 A1* | 12/2007 | Estrella | A61B 5/02055 600/300 |
| 2008/0033252 A1* | 2/2008 | Estrella | A61B 5/0002 600/300 |
| 2008/0129465 A1 | 6/2008 | Rao | |
| 2008/0262562 A1* | 10/2008 | Roberts | H02K 7/1876 607/35 |
| 2008/0300597 A1* | 12/2008 | Morgan et al. | 606/62 |
| 2009/0171448 A1* | 7/2009 | Eli | A61B 17/22 623/1.32 |
| 2010/0160994 A1* | 6/2010 | Feldman | A61N 1/056 607/33 |
| 2010/0167385 A1* | 7/2010 | Celentano et al. | 435/287.1 |
| 2011/0004076 A1 | 1/2011 | Janna et al. | |
| 2011/0270025 A1* | 11/2011 | Fridez et al. | 600/37 |
| 2014/0171156 A1* | 6/2014 | Pattikonda | H04M 1/6041 455/569.1 |

OTHER PUBLICATIONS

PCT Search Report and Written Opinion dated Feb. 26, 2013, International Application No. PCT/US12/069918.

* cited by examiner

IMPLANTED DEVICES AND RELATED USER INTERFACES

CROSS-REFERENCE TO RELATED APPLICATIONS

This application claims benefit of U.S. Provisional Patent Application Ser. No. 61/576,262, filed Dec. 15, 2011, which is hereby incorporated herein by reference.

BACKGROUND OF THE INVENTION

Field of the Invention

Embodiments of the present invention generally relate to electronics and, more specifically, to implanted devices and related user interfaces.

Description of the Related Art

Mobile electronic devices have become an integral part of society. Among other things, mobile electronic devices are now used to play music, place phone calls, send emails, and access information over the Internet. Even though the size of the mobile electronic devices has continued to shrink, carrying a mobile electronic device on a person can still be an inconvenience. For example, a mobile electronic device may be cumbersome in an individual's purse or pocket, or may be damaged easily by not carrying the device in a case, such as a case adapted to fit on an individual's belt. Moreover, mobile electronic devices are frequently misplaced or forgotten when set down, leading to expensive and inconvenient replacements of those mobile electronic devices.

As the foregoing illustrates, there is a need in the art for a more convenient way for individuals to carry mobile electronic devices.

SUMMARY OF THE INVENTION

One embodiment of the invention sets forth a device for implanting beneath human skin. The device includes a processor, a first input device coupled to the processor and adapted to receive input from a user, and a first output device coupled to the processor. The device also includes protective packaging that is disposed around the first input device, the first output device, and the processor so that the device remains protected when implanted below the skin.

One advantage of the disclosed device it that it enables an electronic device to be implanted in a user. Once implanted, the electronic device is present with a user without the user having to cumbersomely carry around the electronic device. Moreover, because the electronic device remains with the user, the user cannot accidentally misplace the electronic devices, and the device is more accessible to the user. In addition, because the electronic device remains with the user, the risk of theft of the electronic devices is reduced.

BRIEF DESCRIPTION OF THE DRAWINGS

So that the manner in which the above recited features of the invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION OF EXEMPLARY EMBODIMENTS

Figure 1:
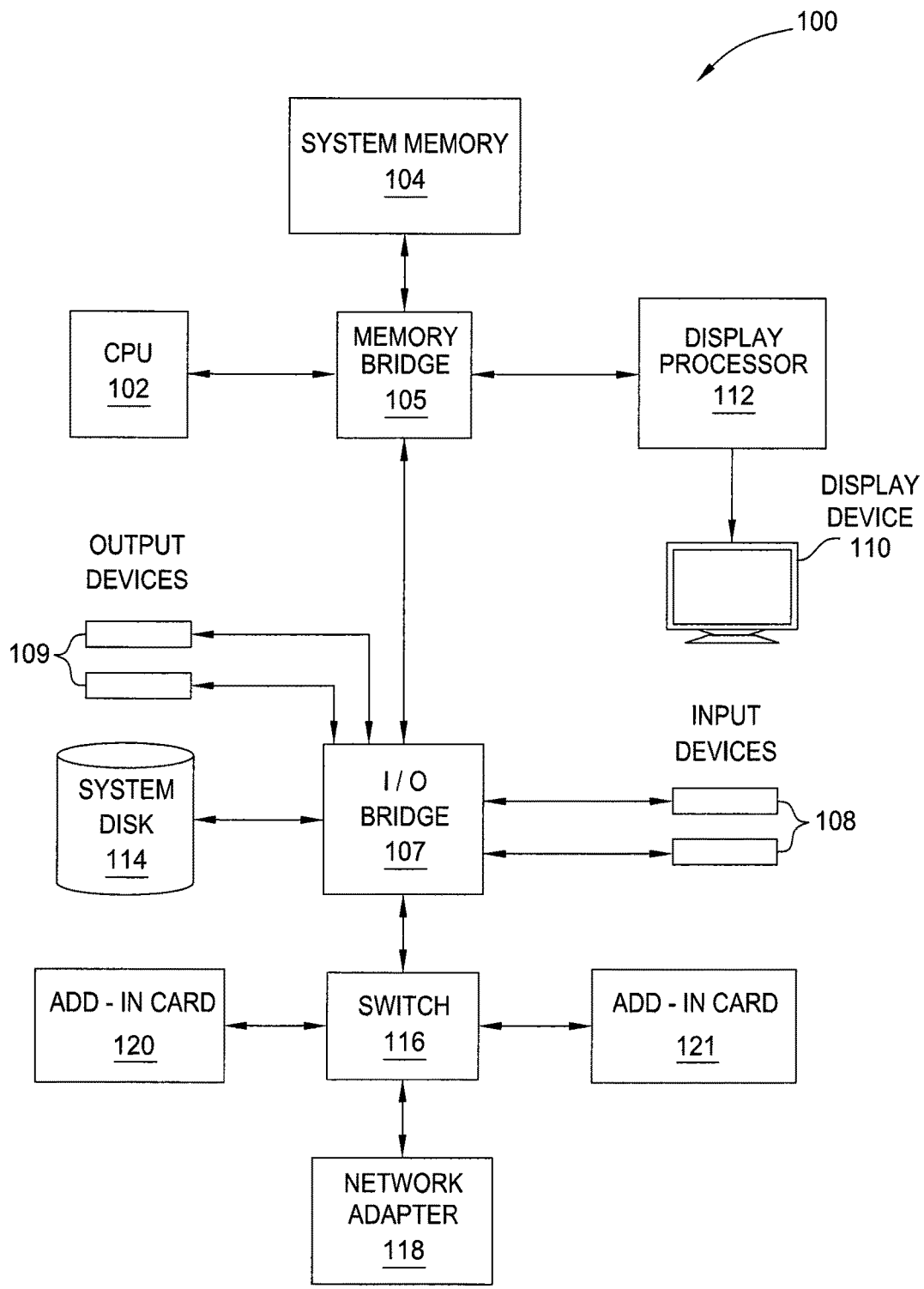
FIG. 1 is a schematic illustration of a system configured to implement one or more aspects of the invention.

FIG. 1 is a schematic illustration of a system 100 configured to implement one or more aspects of the invention. As shown, system 100 includes a central processing unit (CPU) 102 and a system memory 104 communicating via a bus path that may include a memory bridge 105. The CPU 102 includes one or more processing cores, and, in operation, the CPU 102 is the master processor of the system 100, controlling and coordinating operations of other system components. The system memory 104 stores software applications and data for use by the CPU 102. The CPU 102 runs software applications and optionally an operating system. The memory bridge 105, which may be, e.g., a Northbridge chip, is connected via a bus or other communication path (e.g., a HyperTransport link) to an I/O (input/output) bridge 107. The I/O bridge 107, which may be, e.g., a Southbridge chip, receives user input from one or more user input devices 108 (e.g., a tactile button, a tap sensor, a microphone, a pressure sensor, a camera, a motion sensor, and/or a microphone) and forwards the input to CPU 102 via memory bridge 105. The I/O bridge 107 is additionally coupled to one or more output devices, such as a speaker, a light-emitting diode (LED), or a vibrating motor.

An optional display processor 112 is coupled to memory bridge 105 via a bus or other communication path (e.g., a PCI Express, Accelerated Graphics Port, or HyperTransport link). In one embodiment display processor 112 is a graphics subsystem that includes at least one graphics processing unit (GPU) and graphics memory. Graphics memory includes a display memory (e.g., a frame buffer) used for storing pixel data for each pixel of an output image. Graphics memory can be integrated in the same device as the GPU, connected as a separate device with the GPU, and/or implemented within the system memory 104.

The display processor 112 periodically delivers pixels to an optional display device 110 (e.g., a screen or conventional CRT, plasma, LED, OLED, SED or LCD based monitor or television). Additionally, the display processor 112 may output pixels to film recorders adapted to reproduce computer generated images on photographic film. The display processor 112 can provide the display device 110 with an analog or digital signal.

A system disk 114 is also connected to the I/O bridge 107 and may be configured to store content and applications and data for use by the CPU 102 and the display processor 112. The system disk 114 provides non-volatile storage for applications and data and may include fixed or removable hard disk drives, flash memory devices, and CD-ROM, DVD-ROM, Blu-ray, HD-DVD, or other magnetic, optical, or solid state storage devices.

A switch 116 provides connections between I/O the bridge 107 and other components such as a network adapter 118 and various optional add-in cards 120 and 121. The network adapter 118 allows the system 100 to communicate with other systems via an electronic communications network, and may include wired or wireless communication over local area networks and wide area networks such as the Internet.

Other components (not shown), including USB or other port connections may also be connected to I/O bridge 107. For example, an audio processor may be used to generate analog or digital audio output from instructions and/or data provided by CPU 102, system memory 104, or system disk 114. Communication paths interconnecting the various components in FIG. 1 may be implemented using any suitable protocols, such as PCI (Peripheral Component Interconnect), PCI Express (PCI-E), AGP (Accelerated Graphics Port), HyperTransport, or any other bus or point-to-point communication protocol(s), and connections between different devices may use different protocols, as is known in the art.

In one embodiment, the display processor 112 incorporates circuitry optimized for graphics and video processing, including, for example, video output circuitry, and constitutes a graphics processing unit (GPU). In another embodiment, the display processor 112 incorporates circuitry optimized for general purpose processing. In yet another embodiment, the display processor 112 may be integrated with one or more other system elements, such as the memory bridge 105, the CPU 102, and the I/O bridge 107 to form a system on chip (SoC). In still further embodiments, the display processor 112 is omitted and software executed by the CPU 102 performs the functions of the display processor 112.

Pixel data can be provided to the display processor 112 directly from the CPU 102. In some embodiments of the present invention, instructions and/or data representing a scene are provided to a render farm or a set of server computers, each similar to the system 100, via the network adapter 118 or the system disk 114. The render farm generates one or more rendered images of the scene using the provided instructions and/or data. These rendered images may be stored on computer-readable media in a digital format and optionally returned to the system 100 for display. Similarly, stereo image pairs processed by the display processor 112 may be output to other systems for display, stored in the system disk 114, or stored on computer-readable media in a digital format.

Alternatively, CPU 102 provides the display processor 112 with data and/or instructions defining the desired output images, from which the display processor 112 generates the pixel data of one or more output images, including characterizing and/or adjusting the offset between stereo image pairs. The data and/or instructions defining the desired output images can be stored in the system memory 104 or graphics memory within the display processor 112. In an embodiment, the display processor 112 includes 3D rendering capabilities for generating pixel data for output images from instructions and data defining the geometry, lighting shading, texturing, motion, and/or camera parameters for a scene. The display processor 112 can further include one or more programmable execution units capable of executing shader programs, tone mapping programs, and the like.

The CPU 102, render farm, and/or the display processor 112 can employ any surface or volume rendering technique known in the art to create one or more rendered images from the provided data and instructions, including rasterization, scanline rendering REYES or micropolygon rendering, ray casting, ray tracing, image-based rendering techniques, and/or combinations of these and any other rendering or image processing techniques known in the art.

It will be appreciated that the system shown herein is illustrative and that variations and modifications are possible. The connection topology, including the number and arrangement of bridges, may be modified as desired. For instance, in some embodiments, the system memory 104 is connected to the CPU 102 directly rather than through a bridge, and other devices communicate with the system memory 104 via the memory bridge 105 and the CPU 102. In other alternative topologies the display processor 112 is connected to the I/O bridge 107 or directly to the CPU 102, rather than to the memory bridge 105. In still other embodiments, the I/O bridge 107 and the memory bridge 105 might be integrated into a single chip. The particular components shown herein are optional; for instance, any number of add-in cards or peripheral devices might be supported. In some embodiments, the switch 116 is eliminated, and the network adapter 118 and the add-in cards 120, 121 connect directly to the I/O bridge 107.

FIGS. 2A-2H illustrate examples of electronic devices 200A-200H that may be implanted under human skin, according to embodiments of the invention. The electronic devices 200A-200H may include any and all components of the system 100 shown in FIG. 1. The electronic devices illustrated in FIGS. 2A-2H may utilize any number, and any combination, of input and output devices to facilitate user interaction directly with those electronic devices. Examples of input devices include, without limitation, cameras, tactile buttons, tap sensors, microphones, pressure sensors, capacitive sensors, light sensors, and trackballs, any of which may optionally be exposed through human skin or be implanted beneath human skin. In one example, a pressure sensor includes a voltage divider, a 10 kilo-ohm resistor, and a 0.2 inch circular force sensor resistor adapted to sense a weight of about 100 grams to about 10 kilograms. In another example, the capacitive sensor may be a 24-bit, 2-channel capacitance to digital converter. A light sensor may utilize a voltage divider with a 12 millimeter cadmium sulfide 10 mega-ohm photoresistor and a 10 kilo-ohm resistor. Examples of output devices include LEDs, speakers, and vibrating motors.

Moreover, the electronic devices illustrated in FIGS. 2A-2H may include additional sensors, such as magnetic sensors or accelerometers. The electronic devices may include supporting hardware such as units for sending and receiving BLUETOOTH® (e.g., IEEE 802.15.1) or WiFi, ports for receiving data or power, or ports for otherwise facilitating tethering with external devices.

Figure 2A:
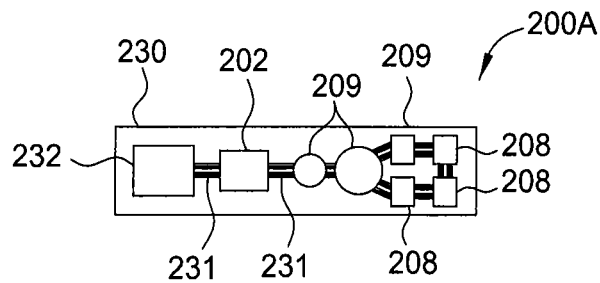
FIGS. 2A-2H illustrate examples of electronic devices that may be implanted under human skin, according to embodiments of the invention.

FIG. 2A illustrates an electronic device 200A for implanting under human skin, according to an embodiment of the invention. The electronic device includes a substrate 230 for supporting components, such as input devices 208 and output devices 209, thereon. The substrate 230 is a flexible circuit having electrical interconnects 231 thereon for electrically coupling components disposed on the substrate 230. It is contemplated, however, that other substrates, such as printed circuit boards, may also be used. Additionally, more electrical interconnects 231 may be utilized to facilitate the desired connections between components of the electronic device 200A.

Three input devices 208 and three output devices 209 are disposed on the electronic device 200A. In one example, the three input devices 208 may include a tap sensor, a tactile button, and a pressure sensor. The tactile button may, for example, offer tactile and audible feedback to a user to indicate that input has been received. The pressure sensor may be capable of determining an amount input pressure from a user, and thus, the electronic device 200A may perform different actions in response to different amounts of pressure received by the pressure sensor. While the electronic device 200A is shown having three input devices 208, more or less input devices are contemplated.

As shown, the electronic device 200A also includes three output devices 209. The output devices 209 communicate visually, audibly, or physically with a user. For example, one of the output devices 208 may be a speaker through which information is audibly conveyed to the user. Another of the output devices 208 may be an LED light or screen through which information is conveyed to a user. A third output device 208 may be a vibrating motor which physically vibrates. While three output devices 208 are shown and described, more or less output devices 208 are contemplated.

The electronic device 200A also includes a processor 202, such as a microcontroller, coupled to the input devices 208 and the output devices 209 via electrical interconnects 231. The processor 202 processes input data received from the input devices 208 and sends output data to the output devices 209. A power source 232, such as battery, is coupled to the input devices 208, the output devices 209, and the processor 202 to facilitate powering of the components of the electronic device 200A. The power source 232 may be a rechargeable battery capable of being recharged using a conductive charger (or other wireless charger) or a recharging cable. In another embodiment, the power source 232 may be a device adapted to harness power from body functions, such as heart beats, or from body heat. If the power source 232 is rechargeable using a recharging cable, a connecting port coupled to the power source 232 may be exposed through the user's skin to facilitate charging of the power source 232. Alternatively, the power source 232 may be a disposable battery, such as a lithium or lithium polymer battery, having a useful life of about six years to about ten years. It is contemplated that when a user is not interacting with the electronic device 200A, the electronic device 200A may operate in a lower power consumption mode to preserve battery life.

The electronic device 200A is adapted to perform many functions of conventional electronic devices; however, the electronic device 200A is capable of performing these functions while implanted beneath the skin of a user. The electronic device 200A may be adapted to set and provide notifications and reminders, store data, display the current time, play digital music, among other functions. The electronic device 200A may also be adapted to place and receive phone calls, text messages, and emails. One skilled in the art will appreciate that electronic device 200A may be adapted to perform additional functions.

Figure 2B:
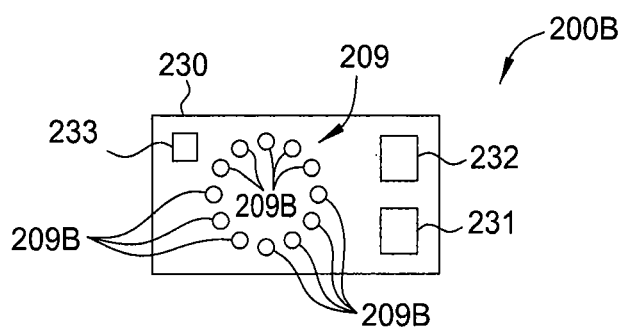

FIG. 2B illustrates an electronic device 200B, according to another embodiment of the invention. The electronic device 200B is an implantable watch that displays the current time to a user. The electronic device 200B includes a processor 231, a power source 232, and a sensor 233, such as an accelerometer. The sensor 233 is adapted to sense a motion or orientation of the electronic device 200B, and provide motion or orientation data to the processor 231. In response, the processor 231 provides data to the output device 209. The output device 209 includes 12 LEDs 209B arranged in circular pattern and spaced about 30 degrees from one another.

In one example, the electronic device 200B is implanted on the forearm or wrist of a user. The sensor 233 is adapted to sense when the electronic device 200B is oriented towards a user's face. In response to the electronic device 200B being oriented toward the user's face, the processor 233 lights two of the LEDs 208B of the output device 209. A first LED 209B of the output device 209 corresponds to the position of an hour hand on a clock face, while the second LED 209B corresponds to the position of a minute hand on the clock face. One of the first or the second LEDs 209B may flash or blink while the other remains continuously lit to distinguish the two. The LEDs 209B of the output device 209 may remain lit for a predetermined amount of time, such as five or ten seconds. It is to be noted that electrical interconnects 231 are not shown in FIG. 2B for clarity purposes. In another embodiment, it is contemplated that a display of the current time on the output device 209 may be initiated using an input device 208 such as a tactile button, rather than through sensing the current orientation of the electronic device 200B using a sensor 233. In such an embodiment, in response to a user pressing a button, the current time would be displayed on the output device 209.

Figure 2C:
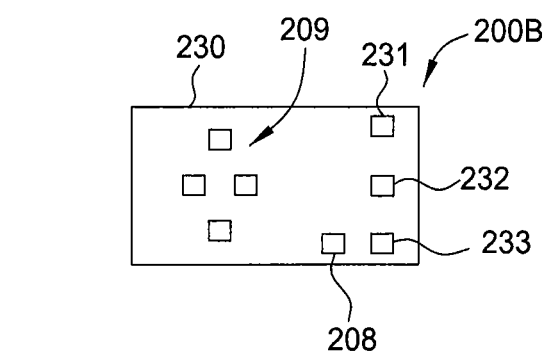

FIG. 2C illustrates an electronic device 200C, according to another embodiment of the invention. As shown, the electronic device 200C is a compass-type device adapted to be implanted beneath the skin of a user. The electronic device includes a processor 231, a battery 232, and a sensor 233, such as a magnetic sensor utilized to sense magnetic north. The electronic device 200B also includes an input device 208, such as a tactile button, and an output device 209, such as four vibrating motors 209C spaced approximately 90 degrees from one another.

The input device 208 receives input from a user, and in response, sends a signal to the processor 231. The processor 231 then retrieves data from the sensor 233, such as data indicating the direction of magnetic north. The processor provides the directional data to the output device 209, and in response, a vibrating motor 209C of the output device 209 vibrates to indicate the direction of magnetic north. If magnetic north is located between two of the vibrating motors 209C of the output device 209, both the vibrating motors 209C may vibrate with relative intensities to indicate the position of magnetic north therebetween. In another embodiment, more than four vibrating motors 209C may be utilized. In yet another embodiment, different output devices, such as LEDs, may be utilized to indicate the direction of magnetic north. It is to be noted that electrical interconnects are not shown in FIG. 2C for clarity purposes.

Figure 2D:
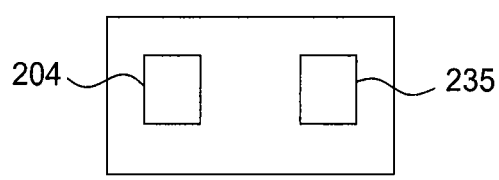

FIG. 2D illustrates an electronic device 200D, according to one embodiment of the invention. The electronic device 200D is an implantable memory storage drive. The electronic device 200D includes a memory unit 204 coupled to a port 235, such as a USB port or other data transfer port. The electronic device 200D is a passive device that receives power through the port 235 when coupled to another device. Thus, the electronic device 200D does not require a battery. If order to facilitate connection between the electronic device 200D and an external device, the port 235 is exposed through the skin of the user, while the remainder of the electronic device 200D is positioned beneath the skin of the user. Thus, only portions of the electronic device 200D requiring external tethering are exposed, and the electronic device 200D remains substantially concealed and unnoticeable. It is to be noted that electrical interconnects are not shown in FIG. 2D for purposes of clarity.

Figure 2E:
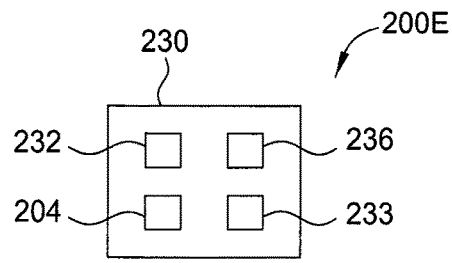

FIG. 2E illustrates an electronic device 200E, according to one embodiment of the invention. The electronic device 200E is an implantable wireless syncing device adapted to provide users with mobile and wireless storage and synchronization capability. The electronic device 200E is capable of storing digital information, such as photos or contact information, thereon. The electronic device includes a power source 232, a memory unit 204, and a BLUETOOTH® chip 236. The BLUETOOTH® chip 236 facilities the transfer of data stored on the memory unit 204 and an external computing device.

The electronic device 200E also includes a sensor 233, such as an accelerometer. The sensor 233 is adapted to detect a specific motion, such as a predetermined synchronous motion, of the electronic device 200E. When the synchronous motion is performed within the signal range of another electronic device 200E having BLUETOOTH® capability, sharing of data between the electronic devices 200E is enabled or performed. It is contemplated that specific synchronous motions may be utilized to exchange different types of information. For example, a first synchronization motion shares a first type of data, such as photos, while a second synchronization motion shares a second type of data, such as contact information. It is to be noted that electrical interconnects are not shown in FIG. 2E for clarity purposes.

Figure 2F:
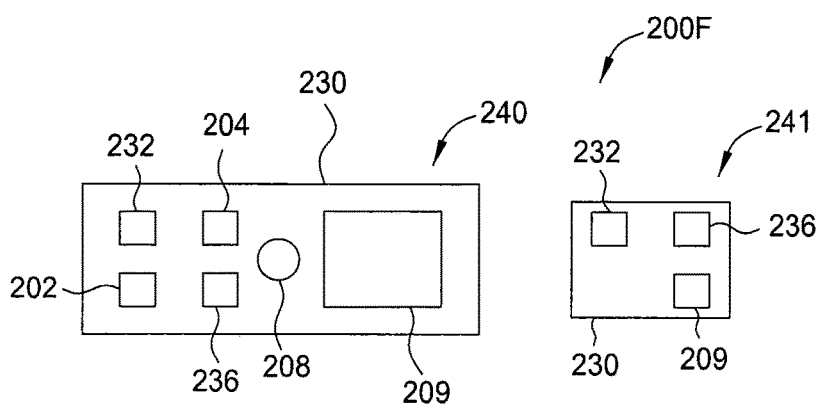

FIG. 2F illustrates an electronic device 200F, according to one embodiment of the invention. As shown, the electronic device 200F is a digital music player having a control unit 240 and a speaker unit 241. The control unit 240 and the speaker unit 241 are adapted to be implanted in separate areas of a user's body, such as in an arm and an earlobe. The control unit 240 and the speaker unit 241 communicate using BLUETOOTH® chips 236 located in each of the units.

The control unit 240 includes a power source 232, a processor 202, a memory unit 204, and a BLUETOOTH® chip 236. The control unit 240 also includes an input device 208, such as a trackball, that is adapted to be exposed through the skin of a user. The control unit 204 also includes an output unit 209, such as a four-color LED screen, for displaying information, such as track selection, thereon. The four-color LED may also optionally be exposed through the skin of the user. Digital music is stored in the memory unit 204 of the control unit 240, and is selected for play using the input device 208. The selected music is sent via BLUETOOTH® to the speaker unit 241.

The speaker unit 241 includes a BLUETOOTH® chip 236 for receiving data from the control unit 240, an output device 209 such as a speaker for outputting the music, and a power source 232 for powering the speaker unit 241. The volume level of the output device 209 is controlled using the control unit 240. It is to be noted that electrical interconnects are not shown in FIG. 2F for clarity purposes. As illustrated by FIG. 2F, multiple devices may be implanted with a single user, and communication therebetween may be facilitated wirelessly, such as via BLUETOOTH®.

Figure 2G:
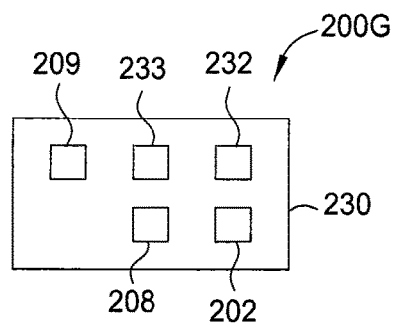

FIG. 2G illustrates an electronic device 200G, according to one embodiment of the invention. The electronic device 200G is an implantable WiFi sensor. The electronic device 200G includes a power source 232 for powering the device, a sensor 233, such as a WiFi sensor, and a processor 202 for processing input signals, output signals, and data received from the sensor 233. The electronic device 200G also includes an input device 208, such as a tactile button, and an output device 209, such as a vibrating motor. The input device 208 receives input from a user, and in response, a signal is sent to the processor 202. Upon receiving the signal from the input device 208, the processor 202 queries the sensor 233 regarding the signal strength of nearby publicly available WiFi networks. The processor 202 then sends a signal to the output device 209, which provides output corresponding to the strength of the signal of a publicly available WiFi network. For example, the output device 209 may be a vibrating motor which vibrates more intensely for stronger WiFi signals, and less intensely for weaker WiFi signals. It is to be noted that electrical interconnects are not shown in FIG. 2G for clarity purposes.

Figure 2H:
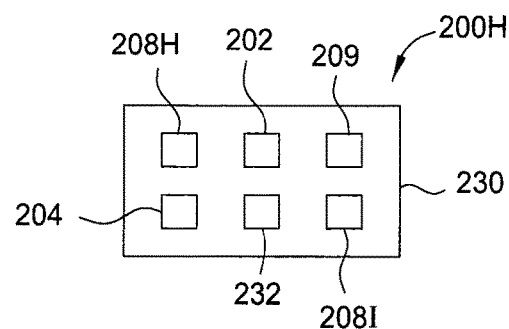

FIG. 2H illustrates an electronic device 200H, according to one embodiment of the invention. The electronic device 200H is an implantable voice recorder. The electronic device 200H includes an input device 208H, such as a microphone for receiving audio input, and an input device 208I, such as a tap sensor, that receives input, and, in response, prompts the input device 208H to begin receiving audio input. A processor 202 processes the audio input from the input device 208H and stores the audio input in the memory unit 204. The stored audio is output through the output device 209 in response to receiving a predetermined gesture at the input device 208I. For example, a single tap on the output device 208I may be utilized to initiate recording of audio through the input device 208H, while a double tap may be utilized to initiate playback of recorded audio through the output device 209. The electronic device 200H also includes a power source 232 for powering the electronic device 200H. It is to be noted that electrical interconnects are not shown in FIG. 2H for clarity purposes.

FIGS. 2A-2H illustrate multiple electronic devices 200A-200H; however, additional electronic devices for performing functions other than those described above are contemplated. One skilled in the art will appreciate that a variety of mobile electronic devices may be implanted under human skin, and interaction therewith may be facilitated using the input devices and output devices described above. Moreover, multiple implanted devices may communicate with one another, either in the same person, or across different people.

Figure 3A:
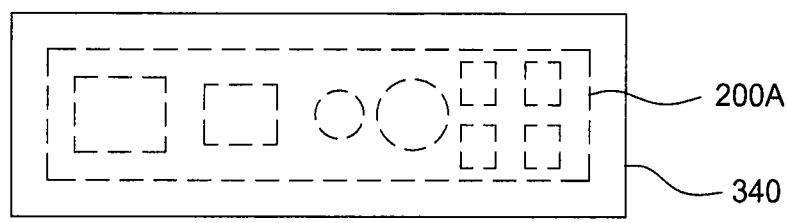
FIGS. 3A and 3B illustrate respective top and side views of an electronic device positioned in a protective packaging, according to one embodiment of the invention.
Figure 3B:
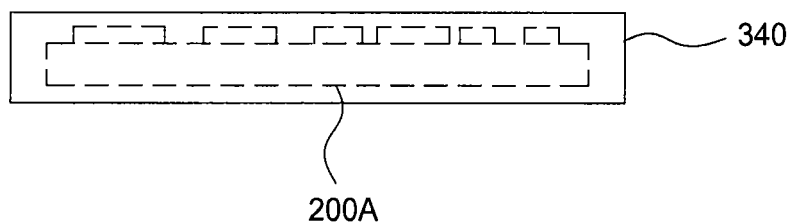

FIGS. 3A and 3B illustrate respective top and side views of an electronic device 200A positioned in a protective packaging 340, according to one embodiment of the invention. The protective packaging 340 is disposed around the electronic device 200A (the electronic device shown with phantom lines) to prevent contact of bodily fluids with the electronic device 200A, and to reduce the immunological response to the electronic device 200A. In embodiments where the electronic device may include a port for accepting an external cable, such as a charging cord, the protective packaging 340 may include an opening to accommodate connection with the port. In such an embodiment, the protective packaging 340 would be sealed around the port to prevent the contact of bodily fluids with the electronic device 200A.

In one example, the protective packaging 340 may be formed from elastomeric silicone which has a low incidence of reaction when implanted within human skin. However, it is contemplated that other pharmacologically inert and non-toxic shell materials may also be utilized, including titanium. In one embodiment, the protective packaging 340 has a thickness within a range of about 0.05 millimeters to about 1.0 millimeters. However, as a general matter, the thickness of the protective packaging 340 is selected to sufficiently withstand user input (such as pressing of tactile buttons), while still allowing a user to detect and distinguish the input devices of the electronic device 200A by palpating the skin above the electronic device 200A. Thus, other materials and dimensions are within the scope of the invention. It is further contemplated that more than one protective packaging 340 may be utilized to further reduce the likelihood that bodily fluids will contact the electronic device 200A. Moreover, the protective packaging 340 may be formed from multiple materials. While FIGS. 3A and 3B are described with respect to the electronic device 200A, it is to be understood that the electronic device 200A is merely illustrative and that any electronic device may be positioned within a protective packaging 340.

Embodiments of the present invention include electronic devices implanted under human skin, for example, between the dermis layer and above underlying subcutaneous fatty tissue. A user is capable of directly interacting with the implanted electronic device through the skin of the user. The electronic devices include one or more input devices such as a tactile button, a tap sensor, a microphone, and a pressure sensor to receive user input. The electronic devices may also include one or more output devices such as an LED, a vibration motor, and a speaker to facilitate output to a user. The implanted devices are encased a protective packaging to reduce immunological responses to the electronic device, and to reduce contact between the electronic device and tissue fluid. The protective packaging allows a user to interact with the one or more input devices.

Each implanted device also includes a battery, which may be integrated therewith, for powering respective implanted devices. The battery may be a replaceable battery having a useful life of about six years to about 10 years. Alternatively, the battery may be a rechargeable battery that is capable of being charged via inductive charging through the skin of a user.

One advantage of the disclosed device it that it enables an electronic device to be implanted in a user. Once implanted, the electronic device is present with a user without the user having to cumbersomely carry around the electronic device. Moreover, because the electronic device remains with the user, the user cannot accidentally misplace the electronic devices, and the device is more accessible to the user. In addition, because the electronic device remains with the user, the risk of theft of the electronic devices is reduced.

Various embodiments of the invention may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored.

The invention has been described above with reference to specific embodiments and numerous specific details are set forth to provide a more thorough understanding of the invention. Persons skilled in the art, however, will understand that various modifications and changes may be made thereto without departing from the broader spirit and scope of the invention. The foregoing description and drawings are, accordingly, to be regarded in an illustrative rather than a restrictive sense.

In view of the foregoing, the scope of embodiments of the present invention is defined by the claims that follow.

What is claimed is:

1. A device configured to be implanted beneath human skin, the device comprising:
   a processor;
   a first input device coupled to the processor and adapted to receive direct input from a user;
   a first output device coupled to the processor, wherein the first output device comprises a first motor that vibrates with a first intensity, wherein a difference between the first intensity and a second intensity of vibration indicates at least one of a spatial direction and a signal intensity; and
   a protective packaging disposed around at least the first input device, the first output device, and the processor.

2. The device of claim 1, wherein the protective packaging comprises elastomeric silicone.

3. The device of claim 2, further comprising a port for coupling a charging cable to the device.

4. The device of claim 3, wherein the protective packaging includes an opening adjacent to the port.

5. The device of claim 1 further comprising a power supply that comprises a battery that supplies power to at least one of the processor, the first input device, and the first output device.

6. The device of claim 5, wherein the battery is rechargeable via capacitive charging.

7. The device of claim 5, wherein the battery comprises a lithium polymer battery.

8. The device of claim 1, wherein the first output device includes a light emitting display that comprises a light emitting diode display for displaying information to a user.

9. The device of claim 8, wherein the light emitting display device is configured to be viewed through a skin of a user.

10. The device of claim 9, wherein the light emitting display device comprises a plurality of light emitting diodes (LEDs).

11. The device of claim 1, further comprising an audio speaker coupled to the processor.

12. The device of claim 1, further comprising a second motor, wherein the second motor vibrates with the second intensity and the difference between the first intensity and the second intensity indicates the spatial direction of magnetic north.

13. The device of claim 1, wherein the first input device comprises at least one of a button and a pressure sensor for receiving input from a user.

14. The device of claim 1, wherein the first input device comprises a microphone for receiving audio input from a user.

15. The device of claim 1, further comprising a BLUETOOTH chip for sending a receiving Bluetooth signals.

16. The device of claim 1, further comprising an accelerometer to determine an orientation of the device.

17. The device of claim 1, further comprising a second input device, wherein the second input device is adapted to be exposed through human skin.

18. The device of claim 17, wherein the second input device comprises a trackball for receiving user input.

19. A device configured to be implanted beneath human skin, the device comprising:
   a processor;
   a memory coupled to the processor and configured to store data;
   a network card coupled to the processor and configured to transfer data between the memory and a second device; and
   a sensor coupled to the processor and adapted to detect a first motion of the device and a second motion of the device, wherein the first motion is associated with a first synchronous type of motion and the second motion is associated with a second synchronous type of motion, wherein, in response to the first motion being detected, data having a first data type is transferred between the memory and the second device, and wherein, in response to the second motion being detected, data having a second data type is transferred between the memory and the second device.

20. A device configured to be implanted beneath human skin, the device comprising:

a processor;

a sensor coupled to the processor and configured to detect a first orientation of the device;

an output device coupled to the processor and configured to display a time when the device is in the first orientation;

a first LED configured to emit first light for a predetermine period of time to display an hour hand associated with the time on the output device; and a second LED configured to emit second light for the predetermine period of time to display a minute hand on the output device, wherein the first LED remains continuously lit for the predetermined period of time and the second LED flashes during the predetermined period of time.

21. The device of claim 20, wherein the hour hand and the minute hand are displayed on a clock face displayed on the output device.

* * * * *